United States Patent [19]
Koenig et al.

[11] Patent Number: 5,525,619
[45] Date of Patent: Jun. 11, 1996

[54] 1,3,4-OXADIAZOL-2(3H)-ONE DERIVATIVES, THEIR PREPARATION AND THEIR THERAPEUTIC APPLICATION

[75] Inventors: Jean-Jacques Koenig, Maisons Laffitte; Samir Jegham, Argenteuil; Frédéric Puech, Rueil Malmaison; Philippe Burnier, Maisons Laffitte, all of France

[73] Assignee: Synthelabo, Le Plessis Robinson, France

[21] Appl. No.: 348,067

[22] Filed: Nov. 23, 1994

[30] Foreign Application Priority Data

Nov. 26, 1993 [FR] France ...................... 9314151

[51] Int. Cl.⁶ .................. C07D 271/113; A61K 31/41
[52] U.S. Cl. ............................. 514/364; 548/144
[58] Field of Search ................. 548/144; 514/364

[56] References Cited

FOREIGN PATENT DOCUMENTS

| 0348257 | 12/1989 | European Pat. Off. |
| 3066056 | 3/1991 | Japan. |
| 9108201 | 6/1991 | WIPO. |

OTHER PUBLICATIONS

European Journal of Medicinal Chemistry, Chimica Therapeutica, vol. 25, 1990, Paris, pp. 659–671, F. Mazouz et al '5–Aryl–1 . . .

Chemical Abstracts, vol. 81, No. 3, 22 Jul. 1974, Abstract No. 12679p.

Agricultural and Biological Chemistry, vol. 47, No. 4, 1983, pp. 701–706, Kamizono et al 'Synthesis and bioligical activity . . .

Journal of Heterocyclic Chemistry, vol. 29, No. 5, 1992, pp. 1081–1084, Milcent et al 'Cyclic transformations of 5–aryl . . .

Journal of Heterocyclic Chemistry, vol. 30, No. 4, 1993, pp. 905–908, Milcent et al. 'Synthesis of 3–acylamino–2–oxazolidi . . .

Bulletin DE DA Societe Chimique de France, No. 1, 1973, pp. 254–258, Golfier et al 'Rearrangement sigmatropiques, 1,3, . . .

Journal of Medicinal Chemistry, vol. 36, No. 9, 1993, pp. 1157–1167, Mazouz et al '5–[4–(Benzyloxy)phenyl] . . .

*Primary Examiner*—Robert Gerstl
*Attorney, Agent, or Firm*—Jacobson, Price, Holman & Stern

[57] ABSTRACT

1,3,4-Oxadiazol-2(3H)-one derivatives, of formula

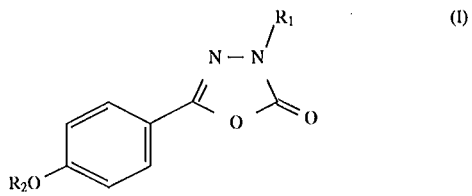

in which

R₁ represents either a hydrogen atom or a linear or branched ($C_{1-4}$)alkyl group which is substituted with a hydroxyl group, a phenoxy group, a ($C_{1-4}$)alkoxy group, a ($C_{1-4}$)alkylthio group, a mercapto group, a ($C_{1-4}$)alkoxy-($C_{1-4}$)alkoxy group, a di($C_{1-4}$)alkylamino group or an N-($C_{1-4}$)alkyl-N-propynylamino group, or represents a ($C_{3-4}$)alkynyl group, and R₂ either represents a linear or branched ($C_{1-8}$)alkyl group which is substituted with one or more halogen atoms and/or a hydroxyl group, a 1-imidazolyl group or a 3-tetrahydropyranyl group, or represents a trifluoro($C_{3-5}$)alkenyl group, in the form of pure enantiomers or mixtures of enantiomers, including racemic mixtures, as well as the addition salts thereof with pharmaceutically acceptable acids, are useful as inhibitors of monoamine oxidase B.

9 Claims, No Drawings

1,3,4-OXADIAZOL-2(3H)-ONE DERIVATIVES, THEIR PREPARATION AND THEIR THERAPEUTIC APPLICATION

The present invention provides 1,3,4-oxadiazol-2(3H)-one derivatives of formula

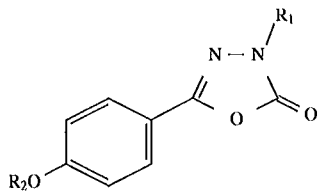

in which

- $R_1$ represents either a hydrogen atom or a linear or branched $(C_{1-4})$alkyl group which is substituted with a hydroxyl group, a phenoxy group, a $(C_{1-4})$alkoxy group, a $(C_{1-4})$alkylthio group, a mercapto group, a $(C_{1-4})$alkoxy-$(C_{1-4})$alkoxy group, a di$(C_{1-4})$alkylamino group or an N-$(C_{1-4})$alkyl-N-propynylamino group, or represents a $(C_{3-4})$alkynyl group, and
- $R_2$ represents either a linear or branched $(C_{1-8})$ alkyl group which is substituted with one or more halogen atoms and/or a hydroxyl group, a 1-imidazolyl group or a 3-tetrahydropyranyl group, or represents a trifluoro$(C_{3-5})$alkenyl group.

The compounds of formula (I) form addition salts with pharmaceutically acceptable acids, these salts also forming part of the invention.

Some compounds of formula (I) contain an asymmetric carbon atom and may therefore exist in the form of pure enantiomers or mixtures of enantiomers, which also form part of the invention.

The present invention also provides a process for the preparation of a compound of formula (I) in which $R_1$ does not represent a hydrogen atom by reacting a compound of formula

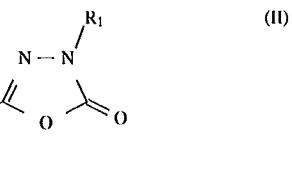

in which $R_1$ is defined as above, provided that $R_1$ does not represent a hydrogen atom, with a compound of formula $R_2X$, in which $R_2$ is defined as above and X represents a halogen atom or the mesyloxy or tosyloxy group, in the presence of a base such as potassium carbonate or sodium hydride, in a solvent such as acetonitrile or dimethylformamide.

The present invention also provides a process for the preparation of a compound of formula (I) in which $R_1$ does not represent a hydrogen atom by reacting a compound of formula (I) in which $R_1$ represents a hydrogen atom, i.e. a compound of formula

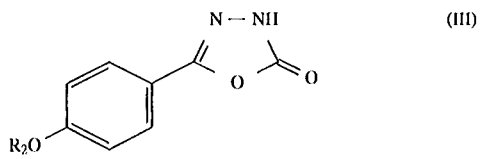

in which $R_2$ is defined as above, with a compound of formula $R_1X$, in which $R_1$ and X are as defined above, provided that $R_1$ does not represent a hydrogen atom, in the presence of a base such as potassium carbonate or sodium hydride, in a solvent such as dimethylformamide.

The compounds of formulae (II) and (III) may be prepared according to methods represented in the following reaction scheme which are similar to those described in International Patent Application No. PCT/FR 90/00847:

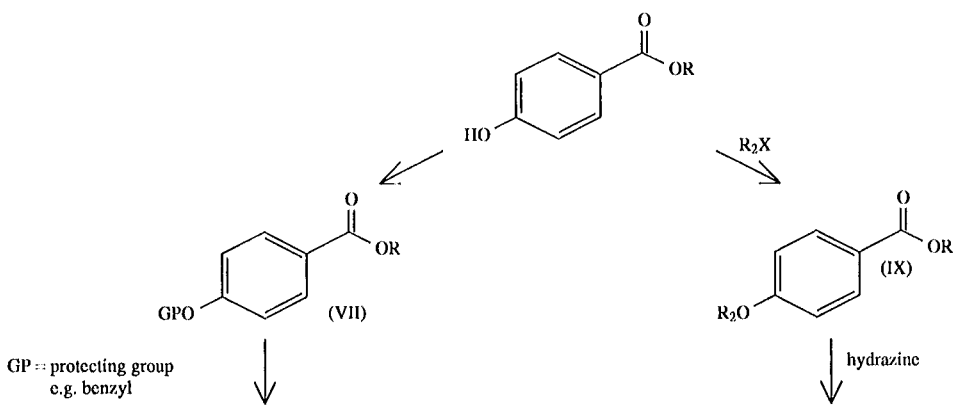

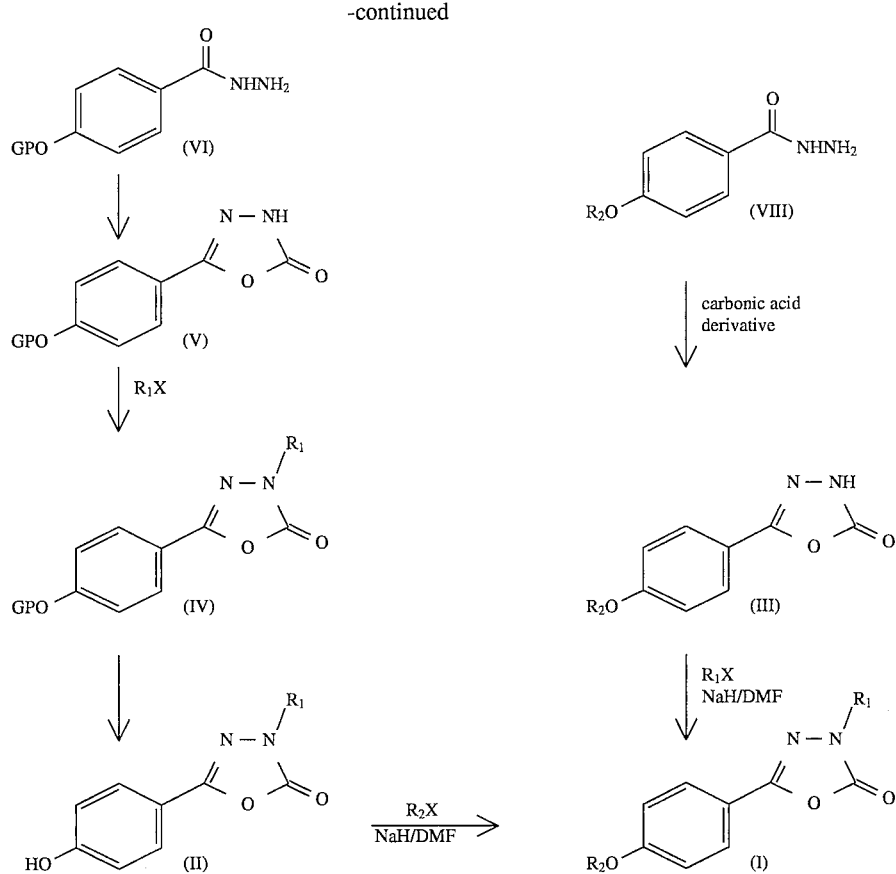

The method for preparing the compounds of formula (II) comprises protecting the hydroxyl group of a p-hydroxybenzoic acid ester with a protecting group such as the benzyl group, and reacting the compound of formula (VII) thus obtained with hydrazine in order to obtain the corresponding hydrazide of formula (VI), which is treated with a carbonic acid derivative, such as phosgene, carbonyldiimidazole or bis(trichloromethyl) carbonate, to give a compound of formula (V), and then with a compound of formula $R_1X$, in which $R_1$ and X are defined as above, to give the compound of formula (IV) which is then deprotected.

The compound of formula (V) in which the protecting group is the benzyl group is a known compound, the preparation of which is described in J. Med. Chem. 36, No. 9, 1157–1167 (1993).

The method for preparing the compounds of formula (III) comprises treating a p-hydroxybenzoic acid ester with a compound of formula $R_2X$, in which $R_2$ and X are defined as above, in reacting the compound of formula (IX) thus obtained with hydrazine and then in treating the hydrazide of formula (VIII) with a carbonic acid derivative such as phosgene, carbonyldiimidazole or bis(trichloromethyl) carbonate.

The present invention accordingly provides a process for the preparation of a compound of formula (I) in which $R_1$ represents a hydrogen atom, comprising treating a hydrazide of formula (VIII) with a carbonic acid derivative such as phosgene, carbonyldiimidazole or bis(trichloromethyl) carbonate.

The Examples which follow illustrate the present invention. The analyses confirm the structure of the compounds of the invention.

EXAMPLE 1

5-[4-(4,4,4-trifluorobutoxy)phenyl]-1,3,4-oxadiazol-2(3H)-one.

1.1 4,4,4-Trifluorobutyl mesylate 16.8 g of 4,4,4-trifluoro-1-butanol and 70 ml of dichloromethane are introduced into a 250 ml three-necked flask. The solution is cooled to 0° C. and 14.6 g of triethylamine and 15.8 g of mesyl chloride are then added. The mixture is stirred for 30 min while being allowed to return to room temperature, then 100 ml of water are added and the organic phase is separated out after settling has taken place. The aqueous phase is extracted with twice 20 ml of dichloromethane, followed by combining the organic phases, drying over sodium sulphate, filtering, evaporating under vacuum at 40° C. and distilling in a bulb oven. 20.8 g of product are obtained.

Boiling point: 155° C. at 1 mm Hg.

1.2 Ethyl 4-(4,4,4-trifluorobutoxy)benzoate 0.77 g of sodium hydride as a 50 % dispersion in oil and 10 ml of dimethylformamide are introduced into a 50 ml three-necked flask and a solution of 2.67 g of ethyl 4-hydroxybenzoate in 20 ml of dimethylformamide is added dropwise to the suspension thus obtained. When the release of gas is complete, 3.32 g of 4,4,4-trifluorobutyl mesylate dissolved in 10 ml of dimethylformamide are added and the mixture is stirred for 24 h at room temperature and is then poured into 300 ml of water. The aqueous phase is extracted with 3 times 150 ml of ethyl acetate and the organic phases are combined, washed with 150 ml of aqueous 1N sodium hydroxide solution and then with 150 ml of water saturated with sodium chloride and evaporated under vacuum. 4.40 g of product are obtained.

Melting point: 60.7° C.

1.3 4-(4,4,4-Trifluorobutoxy)benzoic acid hydrazide 4.40 g of ethyl 4-(4,4,4-trifluorobutoxy)benzoate dissolved in 26 ml of absolute ethanol are introduced into a 50 ml three-necked flask under argon at room temperature. 19.3 ml of hydrazine hydrate are added and the reaction medium is heated to reflux for 20 h. The mixture is then cooled in a bath of ice, and the precipitate formed is filtered off and dried under vacuum. 4.09 g of product are obtained.

Melting point: 130° C.

1.4 5-[4-(4,4,4-Trifluorobutoxy)phenyl]-1,3,4-oxadiazol-2(3H)-one 4.09 g of 4-(4,4,4-trifluorobutoxy)benzoic acid hydrazide, dissolved in 56 ml of hot toluene, are introduced into a 100 ml three-necked flask under nitrogen at room temperature. 12.1 ml of phosgene dissolved in toluene (1.93M) are then added dropwise. The mixture is heated to 100°–110° C. for 1 h 30 min and the excess phosgene is then stripped off using a stream of nitrogen. The reaction medium is cooled and the precipitate formed is filtered off and dried under vacuum. 4.4 g of product are obtained.

Melting point: 187° C.

EXAMPLE 2

5-[4-(4,4,4-trifluorobutoxy)phenyl]-3-methoxyethyl-1,3,4-oxadiazol-2(3H)-one 1.8 g of 5-[4-(4,4,4-trifluorobutoxy)phenyl]-1,3,4-oxadiazol-2(3H)-one, 0.77 g of 2-chloroethyl methyl ether and a solution of 2.15 g of potassium carbonate in 20 ml of dimethylformamide are introduced into a 25 ml three-necked flask. The mixture is heated to 100° C. for 1 h 45 min and is then cooled and poured into 100 ml of water. The precipitate formed is drained, washed with 3 times 50 ml of water and then dissolved in ethyl acetate. The solution is dried over sodium sulphate and filtered, and the solvent is evaporated off. 1.8 g of product are obtained, which product is recrystallized in 10 ml of 96 % ethanol. 1.5 g of product are finally obtained.

Melting point: 105.6° C.

EXAMPLE 3

5-[4-(tetrahydropyran-3-ylmethoxy)phenyl]-3-methoxyethyl-1,3,4-oxadiazol-2(3H)-one 3.1 5-(4-Benzyloxyphenyl)-3-methoxyethyl-1,3,4-oxadiazol-2(3H)-one To a suspension of 15.2 g of sodium hydride (as a 50 % dispersion in oil) in 30 ml of dimethylformamide is added dropwise a solution of 70.9 g of 5-(4-benzyloxyphenyl)-1,3,4-oxadiazol-2(3H)-one in 600 ml of dimethylformamide. The temperature rises to 40° C. The mixture is stirred for 30 min, followed by dropwise addition of a solution of 26.5 ml of 2-chloroethyl methyl ether in 60 ml of dimethylformamide. The mixture is heated to 100° C. and this temperature is maintained overnight, then part of the dimethylformamide is evaporated off, the mixture is filtered and the filtrate is poured into water and extracted with ethyl acetate. The ethyl acetate phase is then evaporated and the residual oil is taken up in hot butanol. After cooling, 71 g of product are recovered.

Melting point: 107° C.

3.2 5-(4-Hydroxyphenyl)-3-methoxyethyl-1,3,4-oxadiazol-2(3H)-one 71 g of 5-(4-benzyloxyphenyl)-3-methoxyethyl-1,3,4-oxadiazol-2(3H)-one in a mixture of 700 ml of tetrahydrofuran and 300 ml of methanol are hydrogenated for 4 hours under reduced pressure in the presence of 8 g of 10% palladium-on-charcoal containing 50% of water and 5 ml of hydrochloric ethanol. The reaction mixture is then filtered on silica and the filtrate is concentrated under reduced pressure. Toluene is added to the residue, and the mixture is then re-evaporated. The product obtained is triturated in ether, filtered off and dried. 50.7 g of product are obtained.

Melting point: 123° C.

3.3 3-Hydroxymethyltetrahydropyran 5 g of 3-formyltetrahydropyran (prepared according to the process described in U.S. Pat. No. 5,149,821) are dissolved in a 60/4 mixture of dichloromethane and methanol, followed by cooling to a temperature between 0° and −5° C. and addition of 0.831 g of sodium borohydride in 8 portions. When the addition is complete, the mixture is allowed to warm to 10° C. and is left at this temperature for 40 min.

The mixture is then cooled to 0° C. and a mixture of 20 ml of water and 2 ml of hydrochloric acid is then added dropwise. The temperature rises to 10° C. The phases are separated after settling has taken place and the aqueous phase is extracted with 6 times 25 ml of dichloromethane, dried over sodium sulphate and filtered, and the solvent is evaporated off. 4.13 g of product are obtained.

The aqueous phase, saturated with sodium chloride, is re-extracted with 3 times 30 ml of dichloromethane. A further 0.270 g of product is obtained, giving 4.4 g of product in total.

3.4 3-Tetrahydropyranylmethyl mesylate 4 g of 3-hydroxymethyltetrahydropyran are dissolved in 10 ml of dichloromethane, then 4.12 g of triethylamine are added, the mixture is cooled to a temperature between 0° and −5° C. and a mixture of 2.9 ml of mesyl chloride and 100 ml of dichloromethane is added dropwise. When the addition is complete, the mixture is allowed to warm to room temperature and is left at this temperature for 45 min.

The organic phase is then washed with water until neutral, dried over sodium sulphate and filtered, and the solvent is evaporated off. 5.9 g of product are obtained in the form of an oil.

3.5 5-[4-(Tetrahydropyran-3-ylmethoxy)phenyl]-3-methoxyethyl-1,3,4-oxadiazol-2(3H)-one 2 g of 5-(4-hydroxyphenyl)-3-methoxyethyl-1,3,4-oxadiazol-2(3H)-one are dissolved in acetonitrile, followed by addition of 2.92 g of potassium carbonate and a solution of 3.12 g of 3-tetrahydropyranylmethyl mesylate in acetonitrile. The mixture is heated to reflux for 5 h and then filtered, diluted with ethyl acetate and washed with three times 50 ml of 2N sodium hydroxide. The organic phase is then washed with water until neutral, dried over sodium sulphate and filtered, and the solvent is then evaporated off. After two recrystallizations in diisopropyl ether, 0.7 g of product is obtained.

Melting point: 77° C.

EXAMPLE 4

5-[4-(4,4,4-trifluorobutoxy)phenyl]-3-hydroxyethyl-1,3,4-oxadiazol-2(3H)-one

To a solution of 0.70 g of 5-[4-(4,4,4-trifluorobutoxy)phenyl]-3-methoxyethyl-1,3,4-oxadiazol-2(3H)-one in 10 ml of dichloromethane are added dropwise 1.2 g of boron tribromide. The mixture is left to react overnight and is then treated with aqueous sodium bicarbonate solution and extracted with dichloromethane. The organic phase is washed with water, dried over sodium sulphate and concentrated. The crude product obtained is purified on a column of silica with a 1/1 mixture of ethyl acetate and heptane. 200 mg of product are obtained.

Melting point: 118° C.

EXAMPLE 5

5-[4-(4,4,4-Trifluorobutoxy)phenyl]-3-methylthioethyl-1,3,4-oxadiazol-2(3H)-one 2 g of 5-[4-(4,4,4-trifluorobutoxy)phenyl]-1,3,4-oxadiazol-2(3H)-one, 1.14 g of 2-chloroethyl methyl sulphide, 2.4 g of potassium carbonate and 30 ml of dimethylformamide are introduced into a 50 ml three-necked round-bottomed flask. The reaction mixture is heated to 90° C. and is maintained at this temperature overnight, then poured into water. The precipitate formed is collected by filtration, washed with water and taken up in ethyl acetate. The solution is dried over sodium sulphate and the solvent is then evaporated off. After recrystallization in diisopropyl ether, 1.7 g of product are obtained.

Melting point: 104.7° C.

Various compounds of the invention are presented in the following table with their physical characteristics.

TABLE

| Compound | R1 | R2 | salt/base | m.p. (°C.) |
|---|---|---|---|---|
| 1 | $-CH_2CH_2OCH_3$ | $-(CH_2)_3CF_3$ | base | 105.6 |
| 2 | $-CH_2CH_2OH$ | $-(CH_2)_3CF_3$ | base | 118 |
| 3 | $-CH_2CH_2OC_4H_9$ | $-(CH_2)_3CF_3$ | base | 91.8 |
| 4 | $-(CH_2)_2-N(CH_3)(CH_2C\equiv CH)$ | $-(CH_2)_3CF_3$ | base | 95.3 |
| 5 | H | $-(CH_2)_3CF_3$ | base | 186.9 |
| 6 | $-CH_2CH_2OC_2H_5$ | $-(CH_2)_3CF_3$ | base | 111.1 |
| 7 | $-(CH_2)_2-N(CH_3)_2$ | $-(CH_2)_3CF_3$ | HCl | 176 |
| 8 | $-CH_2C\equiv CH$ | $-(CH_2)_3CF_3$ | base | 125.1 |
| 9 | $-(CH_2)_2O-C_6H_5$ | $-(CH_2)_3CF_3$ | base | 118.1 |
| 10 | $-(CH_2)_2O(CH_2)_2OCH_3$ | $-(CH_2)_3CF_3$ | base | 92.7 |
| 11 | $-CH_2CH_2SCH_3$ | $-(CH_2)_3CF_3$ | base | 104.7 |
| 12 | $-CH_2CH_2OCH_3$ | $CH_3CH_2CH_2CH(OH)CCl_3$ | base | 125.6 |
| 13 | $-CH_2CH_2OCH_3$ | $-CH_2CF_3$ | base | 115 |
| 14 | $-CH_2CH_2OCH_3$ | $-CH_2CH=CHCF_3$ | base | 92.6 |
| 15 | $-CH_2CH_2OCH_3$ | $CH_3CH_2CH_2CH(CH_3)CF_3$ | base | 99 |
| 16 | $-CH_2CH_2OCH_3$ | $-(CH_2)_5CF_3$ | base | 84.8 |
| 17 | $-CH_2CH_2OCH_3$ | $CH_3CH_2CH_2CH_2CH(OH)CF_3^-$ | base | 114.8 |
| 18 | $-CH_2CH_2OCH_3$ | $-(CH_2)_4$-imidazolyl | HCl | 163 |

TABLE-continued

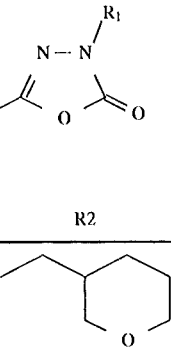

| Compound | R1 | R2 | salt/base | m.p. (°C.) |
|---|---|---|---|---|
| 19 | —CH$_2$CH$_2$OCH$_3$ | 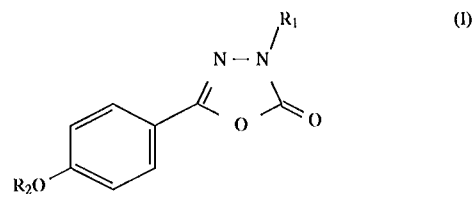 | base | 77 |

HCl = hydrochloride

The compounds of the invention were subjected to pharmacological tests to allow their inhibitory effect on monoamine oxidase to be determined.

These tests involve measuring the in vitro activity of monoamine oxidase-A (MAO-A) and of monoamine oxidase-B (MAO-B).

The MAO-A and MAO-B activity measurements were made using rat brain homogenate as enzyme source. The method used, described by C. Fowler and M. Strolinbenedetti, in J. Neurochem., 40, 1534–1541 (1983), consists of pre-incubating the enzyme for 20 minutes at 37° C. in the presence or absence of the inhibitors studied. After this period, the reaction is started by adding [$^{14}$C]serotonin (5-HT, 125 μM), in order to measure the MAO-A activity, or [$^{14}$C]phenylethylamine (PEA, 8 μM) in order to measure the MAO-B activity. After incubation for 5 minutes at 37° C. in the presence of [$^{14}$C]serotonin 5-HT and for 1 minute at 37° C. in the presence of [$^{14}$C]PEA, the reaction is stopped by adding hydrochloric acid. The metabolites of the amines are then extracted and the radioactivity is quantified by liquid scintillation counting.

The inhibitory activity with respect to MAO-B is given by the inhibition constant Ki (MAO-B).

For the compounds of the invention, Ki (MAO-B) varies between $10^{-6}$ and $10^{-9}$ M.

Moreover, the ratio Ki (MAO-A)/Ki (MAO-B) was calculated. For the compounds of the invention, this ratio is between $10^3$ and $10^4$.

It thus appears that the compounds of the invention have a powerful and selective inhibitory activity towards MAO-B.

The compounds of the invention may thus be used to prepare medicinal products for inhibiting monoamine oxidase B, these medicinal products finding therapeutic use especially in the treatment of neurological disorders associated with pathological ageing, memory disorders, mood disorders, schizophrenia, psychasthenia, slowing of the mind associated with ageing, certain forms of depression and Parkinson's disease.

The compounds of the invention may be provided, in combination with excipients, in the form of formulated compositions for the purpose of oral, parenteral or rectal administration, for example in the form of tablets, sugar-coated tablets, capsules, solutions, suspensions or suppositories.

Via the oral route, the daily dose of active principle administered may be up to 50 mg/kg, in one or more doses. Via the parenteral route, it may be up to 5 mg/kg and, via the rectal route, 10 mg/kg.

We claim:

1. A 1,3,4-oxadiazol-2(3H)-one derivative of formula $$\text{(I)}$$

in which

R$_1$ represents either a hydrogen atom or a linear or branched (C$_{1-4}$)alkyl group which is substituted with a hydroxyl group, a phenoxy group, a (C$_{1-4}$)alkoxy group, a (C$_{1-4}$)alkylthio group, a mercapto group, a (C$_{1-4}$)alkoxy(C$_{1-4}$)alkoxy group, a di(C$_{1-4}$)alkylamino group or an N-(C$_{1-4}$)alkyl-N-propynylamino group, or represents a (C$_{3-4}$)alkynyl group, and R$_2$ either represents a linear or branched (C$_{1-8}$)alkyl group which is substituted with one or more halogen atoms and/or a hydroxyl group, a 1-imidazolyl group or a 3-tetrahydropyranyl group, or represents a trifluoro(C$_{3-5}$)alkenyl group, in the form of a pure enantiomer or a mixture of enantiomers, including racemic mixtures, or a pharmaceutically acceptable acid addition salt thereof.

2. A compound of formula (I) according to claim 1 which is 5-[4-(4,4,4-trifluorobutoxy)phenyl]-3-methoxyethyl-1,3,4-oxadiazol-2(3H)-one.

3. A compound of formula (I) according to claim 1 which is 5-[4-(4,4,4-trifluorobutoxy)phenyl]-3-hydroxyethyl-1,3,4-oxadiazol-2(3H)-one.

4. A compound of formula (I) according to claim 1 which is 5-[4-(4,4,4-trifluorobutoxy)phenyl]-3-methylthioethyl-1,3,4-oxadiazol-2(3H)-one.

5. A compound of formula (I) according to claim 1 which is 5-[4-(4,4,4-trifluoro-2-butenyloxy)phenyl]-3-methoxyethyl-1,3,4-oxadiazol-2(3H)-one.

6. A compound of formula (I) according to claim 1 which is 5-[4-(4,4,4-trifluoro-3(R)-hydroxybutoxy)phenyl]-3-methoxyethyl-1,3,4-oxadiazol-2(3H)-one.

7. A compound of formula (I) according to claim 1 which is 5-[4-(tetrahydropyran-3-ylmethoxy)phenyl]-3-methoxyethyl-1,3,4-oxadiazol-2(3H)-one.

8. A composition comprising a 1,3,4-oxadiazol-2(3H)-one derivative of formula

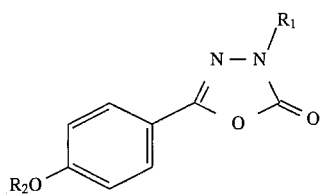 (I)

in which
- $R_1$ represents either a hydrogen atom or a linear or branched $(C_{1-4})$alkyl group which is substituted with a hydroxyl group, a phenoxy group, a $(C_{1-4})$alkoxy group, a $(C_{1-4})$alkylthio group, a mercapto group, a $(C_{1-4})$alkoxy-$(C_{1-4})$alkoxy group, a di$(C_{1-4})$alkylamino group or an N-$(C_{1-4})$alkyl-N-propynylamino group, or represents a $(C_{3-4})$alkynyl group, and
- $R_2$ either represents a linear or branched $(C_{1-8})$alkyl group which is substituted with one or more halogen atoms and/or a hydroxyl group, a 1-imidazolyl group or a 3-tetrahydropyranyl group, or represents a trifluoro$(C_{3-5})$alkenyl group, in the form of a pure enantiomer or a mixture of enantiomers, including racemic mixtures, or a pharmaceutically acceptable acid addition salt thereof, in combination with a pharmaceutically acceptable excipient.

9. A method for treatment of the human or animal body comprising administering a 1,3,4-oxadiazol-2(3H)-one derivative of formula

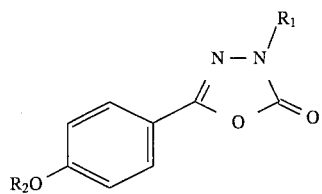 (I)

in which
- $R_1$ represents either a hydrogen atom or a linear or branched $(C_{1-4})$alkyl group which is substituted with a hydroxyl group, a phenoxy group, a $(C_{1-4})$alkoxy group, a $(C_{1-4})$alkylthio group, a mercapto group, a $(C_{1-4})$alkoxy-$(C_{1-4})$alkoxy group, a di$(C_{1-4})$alkylamino group or an N-$(C_{1-4})$alkyl-N-propynylamino group, or represents a $(C_{3-4})$alkynyl group, and
- $R_2$ either represents a linear or branched $(C_{1-8})$alkyl group which is substituted with one or more halogen atoms and/or a hydroxyl group, a 1-imidazolyl group or a 3-tetrahydropyranyl group, or represents a trifluoro$(C_{3-5})$alkenyl group, in the form of a pure enantiomer or a mixture of enantiomers, including racemic mixtures, or a pharmaceutically acceptable acid addition salt thereof, as an inhibitor of monoamine oxidase B.

\* \* \* \* \*